United States Patent [19]
Petersen et al.

[11] 3,936,447
[45] Feb. 3, 1976

[54] 7-ACYLAMINO-DESACETOXY-CEPHALOSPORANIC ACID ESTERS AND THEIR PRODUCTION

[75] Inventors: Uwe Petersen, Cologne; Hans-Joachim Kabbe; Siegfried Petersen, both of Leverkusen, all of Germany

[73] Assignee: Bayer Aktiengesellschaft, Germany

[22] Filed: Mar. 26, 1974

[21] Appl. No.: 454,921

[30] Foreign Application Priority Data
Apr. 19, 1973 Germany............................ 2320040

[52] U.S. Cl............................ 260/243 C; 260/622 P
[51] Int. Cl.² ................ C07D 501/18; C07D 501/10
[58] Field of Search ................................. 260/243 C

[56] References Cited
OTHER PUBLICATIONS
Toshiyasu et al., Chem Abs., 78, 111301d, (1973).

*Primary Examiner*—Nicholas S. Rizzo
*Assistant Examiner*—Mark L. Berch

[57] ABSTRACT

7-Acylamino-desacetoxy-cephalosporanic acid esters are produced by heating a sulfoxide of 6-acylaminopenicillanic acid ester at a temperature of from about 60°C to about 150°C in the presence of a phenol catalyst. The 7-acylamino-desacetoxy-cephalosporanic acid esters produced are known per se and are useful as intermediates for the preparation of desacetoxy-cephalosporin derivatives which exhibit antibacterial activity.

28 Claims, No Drawings

7-ACYLAMINO-DESACETOXY-CEPHALOSPORANIC ACID ESTERS AND THEIR PRODUCTION

The present invention is concerned with a process for the production of 7-acylamino-desacetoxy-cephalosporanic acid esters which compounds are generally known per se and which compounds are useful as intermediates for the preparation of desacetoxycephalosporin derivatives, which derivatives are useful for their anti-bacterial activity, (see E. H. Flynn, Cephalosporins and Penicillins, Academic Press, New York, 1972).

According to U.S. Pat. No. 3,275,626, 7-acylaminodesacetoxy-cephalosporanic acid derivatives are obtained when the correspondingly substituted penicillin-sulphoxide derivatives are rearranged in the presence of acids at an elevated temperature. However, the process of that patent results in mixtures with such a low content of the 7-acylamino-desacetoxy-cephalosporanic acid derivatives that economical use of the process is richly impossible.

German Offenlegungsschrift No. 2,006,689 discloses what is suggested as an improvement of the process of U.S. Pat. No. 3,275,626. According to the German Offenlegungsschrift, by using solvents which contain a tertiary carboxamide, the rearrangement in the presence of sulphonic acids can be carried out with a better yield. However, the process suffers from the disadvantage that the reaction solutions must be heated with the strong acids for several hours.

The present invention provides an improved process for the production of 7-acylamino-desacetoxy-cephalosporanic acid esters. According to the process of the present invention, 7-acylaminodesacetoxy-cephalosporanic acid esters of the formula:

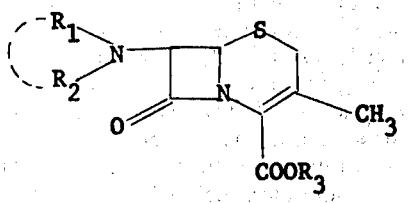

wherein
$R_1$ is hydrogen, and
$R_2$ is phenacetyl, phenoxyacetyl, trityl or α-aminophenacetyl the amino group of which may be protected, and which is unsubstituted or substituted in the phenyl moiety by one or more substituents selected from the group consisting of hydroxy, alkoxy, especially lower alkoxy, alkylmercapto, especially lower alkylmercapto, and halogen; thienylacetyl; or tert.-butoxycarbonyl; or
$R_1$ and $R_2$ together with the nitrogen atom to which they are attached form a phthalimido or succinimido moiety; and
$R_3$ is benzyl, methoxybenzyl, nitrobenzyl, diphenylmethyl, trityl, β,β,β-trichloroethyl, cyanomethyl, 9-fluorenyl, tert.-butyl, phenacyl, chlorophenacyl, bromophenacyl, nitrophenacyl, phenylphenacyl, alkoxyphenacyl, especially lower alkoxyphenacyl, or trimethylsilyl,
which comprises heating a sulfoxide of 6-acylaminopenicillanic acid ester of the formula:

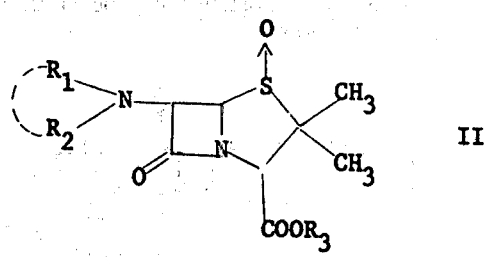

wherein $R_1$, $R_2$ and $R_3$ are as above defined, at a temperature of from about 60°C to about 150°C in the presence of a phenol catalyst of the formula:

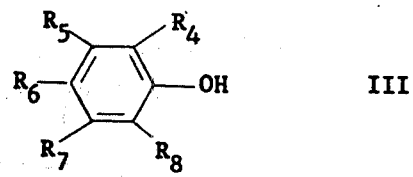

wherein $R_4$, $R_5$, $R_6$, $R_7$ and $R_8$ are the same or different and each is selected from the group consisting of hydrogen, nitro, cyano, halogen (fluorine, chlorine, bromine or iodine, especially chlorine or bromine), alkyl of 1 to 4 carbon atoms, haloalkyl of 1 to 4 carbon atoms wherein the halogen is preferably fluorine, chlorine or bromine, especially fluorine, the preferred haloalkyl moiety being trifluoromethyl, carbalkoxy (-COOalkyl) of 2 to 5 carbon atoms, especially carbomethoxy and carbethoxy, alkylcarbonyl (—COalkyl) of 2 to 7 carbon atoms, alkylsulphonyl (—SO₂alkyl) of 1 to 6 carbon atoms, benzoyl, phenylsulphonyl, carbophenoxy, phenyl or phenyl substituted by one or more substituents selected from the group consisting of nitro, cyano, halogen, alkyl of 1 to 4 carbon atoms, haloalkyl of 1 to 4 carbon atoms, carbalkoxy of 2 to 5 carbon atoms, alkylcarbonyl of 2 to 7 carbon atoms, alkylsulphonyl of 1 to 6 carbon atoms, benzoyl, phenylsulphonyl, carbophenoxy, and phenyl; provided that only one of $R_4$–$R_8$ is halogen and not more than two of $R_4$–$R_8$ is hydrogen.

The 7-acylamino-desacetoxy-cephalosporanic acid derivatives produced above are intermediates and may be converted into desacetoxy-cephalosporin derivatives according to techniques per se known in the art. These final products are useful for treating bacterial infections in humans and animals.

It is distinctly surprising that, according to the above process, the rearrangement of 6-acylaminopenicillanic acid-S-oxide-esters of formula II give 7-acylamino-desacetoxy-cephalosporanic acid esters of formula I when the heating takes place in the presence of a phenol because it would have been expected in the light of the prior art that this rearrangement would only take place in the presence of strong acids, such as sulphonic acids.

The process according to the present invention thus represents a number of advantages, as well as a technical advance of the known process for the production of 7-acylamino-desacetoxycephalosporanic acid esters, and it is especially valuable because it can utilize penicillin-sulphoxide derivatives which are sensitive to strong acids.

If for example phenoxymethylpenicillin-sulphoxide p-nitrobenzyl ester is used as the starting compound, the course of the reaction can be illustrated by the following equation:

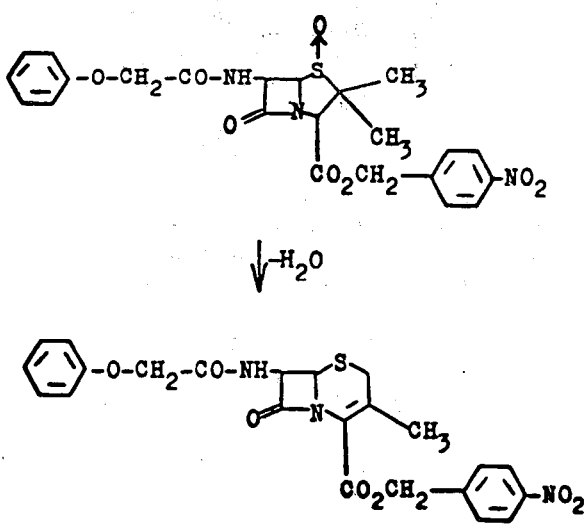

According to one embodiment of the present invention:

$R_1$ is hydrogen;

$R_2$ is phenacetyl, phenoxyacetyl, or α-aminophenacetyl; and $R_3$ is benzyl, p-methoxybenzyl, p-nitrobenzyl, β,β,β-trichloroethyl, cyanomethyl, p-chlorophenacyl, p-nitrophenacyl, or p-phenylphenacyl, provided that, when $R_2$ in formula I is α-aminophenacetyl, $R_2$ in formula II is α-aminophenacetyl having a protective group on the amino moiety which is removed after the reaction, as e.g. 1-methyl-2-benzoyl-vinyl, 1-methyl-2-acetyl-vinyl, 1-methyl-2-alkoxycarbonyl-vinyl, 2.2.2-trichloraethoxycarbonyl-, benzyloxycarbonyl or t-butoxycarbonyl.

Most of the 6β-acylaminopenicillanic acid S-oxide esters of formula II which are used as starting materials according to the present invention are known.

They can be prepared, for example, by oxidation of penicillins to give 6-acylaminopenicillanic-sulphoxide acids and subsequent esterification [J. Amer. Chem. Soc. 91, 1401 (1969)] or by oxidation of 6-acylaminopenicillanic acid esters with suitable oxidizing agents such as sodium metaperiodate, hydrogen peroxide or per-acids.

The reaction is appropriately carried out in the presence of a diluent; preferred diluents used are hydrocarbons, such as benzene, toluene, xylene, cyclohexane and methylcyclohexane halogenated hydrocarbons, such as chloroform, dichloroethane and chlorobenzene; nitro-hydrocarbons, such as nitromethane, nitroethane and nitrobenzene; open chain and cyclic ethers, such as dibutyl ether, tetrahydrofurane, dioxane and ethylene glycol dimethyl ether; ketones, such as methyl isopropyl ketone, methyl isobutyl ketone and cyclohexanone; esters, such as butyl acetate, isoamyl acetate, triethyl phosphate and methanephosphonic acid dimethyl ester; nitriles, such as acetonitrile and propionitrile; amides, such as dimethylformamide, dimethylacetamide, N-methylpyrrolidone and hexamethyl-phosphoric acid tris-amide; tetraalkylureas, such as tetramethylurea, 1-(1-pyrrolidylcarbonyl)-pyrrolidine and N,N-dimethyl-N',N'-tetramethyleneurea; sulphoxides, such as dimethylsulphoxide; and sulphones, such as tetramethylenesulphone, as well as mixtures of these solvents; preferably, mixtures of a non-polar or weakly polar diluent, for example benzene, toluene or methylcyclohexane, with a strongly polar solvent, e.g. amides or sulphoxides, are employed.

The phenol of formula III is preferably used in an amount of 5 – 80, more preferably 20 – 50, mol per cent, based on the S-oxide of formula II employed, but the reaction can also be carried out in the presence of larger amounts of phenol. Representative phenols which may be used as catalysts according to the above described process include:

2-bromo-4,6-dicyano-phenol,
2-iodo-4,6-dicyano-phenol,
2-trifluoromethyl-4,6-dinitro-phenol,
2,4-bis-trifluoromethyl-6-nitro-phenol,
2,4,6-trinitro-phenol,
2-chloro-4,6-dinitro-phenol,
3-chloro-2,6-dinitro-phenol,
3-chloro-4,6-dinitro-phenol,
4-cyano-2-iodo-6-nitro-phenol,
2-carbethoxy-4,6-dinitro-phenol,
4-carbomethoxy-2,6-dinitro-phenol,
4-fluoro-2,6-dinitro-phenol,
2,6-dicyano-4-nitro-phenol, and
2,4,6-tricyano-3,5-di-(phenylsulphonyl)-phenol.

The reaction is carried out at temperatures between 60°C and 150°C, preferably between 80°C and 130°C.

The reaction can be carried out under atmospheric pressure but also under elevated pressure; the reaction conditions are most appropriately so chosen that the reaction can take place under reflux at atmospheric pressure.

In carrying out the process according to the present invention, the methods customary in organic chemistry for removing the water produced in the reaction can be used. Thus the water may be removed for example by azeotropically distilling off the water with the diluent and recycling the latter, or by passing the refluxing portions of the diluent over dehydrating agents, such as anhydrous sodium sulphate, calcium chloride or molecular sieves, or by adding to the batch chemicals which easily react with water, such as ketals, acetals or orthoesters.

The mixture resulting from the reaction can for example be worked up by concentrating the solution almost to dryness and separating the end product and by-products either by recrystallization or by chromatography or by the addition of solvents in which the by-products are soluble. If the catalysts used dissolve in water, it is also possible to add water to the reaction mixture and to extract the cephalosporin derivative formed with a water-immiscible solvent such as toluene or chloroform; the organic part is concentrated and the crude product which remains is purified, for example by recrystallization or by dissolving out the by-products.

Most of the cephalosporin derivatives obtained according to the process of the present invention are known from German Offenlegungsschrift No. 2,012,955. They can be easily differentiated spectroscopically and chromatographically from the starting compounds and from by-products formed.

The following non-limitative examples more particularly illustrate the present invention.

EXAMPLE 1

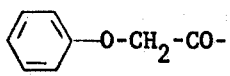

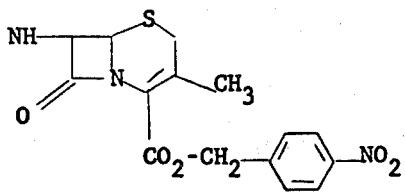

25 g of penicillin-V-sulphoxide p-nitrobenzyl ester (0.05 mol) in 300 ml of toluene and 150 ml of dimethylacetamide, to which 6 ml of acetone-dimethylketal and 5 g of 2-bromo-4,6-dicyano-phenol have been added, are heated for 2-1/2 hours under reflux. The red-brown solution is concentrated to 38 g at 90°/20 mm and 50 ml of methanol are added to the oil which remains. The crystals which precipitate are filtered off and washed with cold methanol and acetonitrile. 16.2 g of 7-phenoxyacetamido-3-methyl-$\Delta^3$-cephem-4-carboxylic acid p-nitrobenzyl ester of melting point 186°–189°C are obtained; it was shown to be identical with authentic material by thin layer chromatography, elementary analysis and infra-red, nuclear resonance and mass spectra. Since 1.4 g of starting compound were recovered from the mother liquor, the total yield is 71% of theory.

EXAMPLE 2

10 g of penicillin-v-sulphoxide p-nitrobenzyl ester (0.02 mol) in 120 ml of toluene and 60 ml of dimethyl-acetamide, to which 2.5 ml of acetone-dimethylketal and 2 g of 2-chloro4,6-dinitro-phenol have been added, are heated for 2½ hours under reflux. Working up is carried out as described in Example 1 and 0.65 g of starting compound is recovered from the mother liquor. Yield: 6.3 g (70% of theory) of 7-phenoxyacetamido-3methyl-$\Delta^3$-cephem-4-carboxylic acid p-nitrobenzyl ester of melting point 186°–189°C.

EXAMPLE 3

10 g of penicillin-V-sulphoxide p-nitrobenzyl ester in 80 ml of benzene and 60 ml of dimethylacetamide are heated with 1.8 g of 4-carbomethoxy-2,6-dinitro-phenol for 12 hours under reflux, the red-brown solution is concentrated to 16.7 g in vacuo, 100 ml of iso- propyl alcohol/ether (1:1) are added to the brown oil which remains and the product is filtered off and washed with a little acetonitrile. 6.6 g (68.5%) of 7-phenoxyacetamido3-methyl-$\Delta^3$-cephem-4-carboxylic acid p-nitrobenzyl ester of melting point 186°–189°C are obtained.

EXAMPLES 4–12

5 g of penicillin-V-sulphoxide p-nitrobenzyl ester in 60 ml of toluene and 30 ml of dimethylacetamide are heated with X g of the phenol indicated in the table for 5 hours under reflux, the mixture is concentrated in vacuo at 90°C and 5 ml of methanol are added to the residue. The 7-phenoxyacetamido-3-methyl$\Delta^3$ -cephem-4-carboxylic acid p-nitrobenzyl ester which precipitates is filtered off, washed with methanol and a little acetonitrile, and dried.

| Example | Catalyst | X (g) | Melting point (°C) | Yield (g) |
|---|---|---|---|---|
| 4 | 2-Trifluoromethyl-4,6-dinitrophenol | 1.0 | 186–188 | 2.6 |
| 5 | 2,4-bis-Trifluoromethyl-6-nitrophenol | 1.0 | 185–188 | 1.4 |
| 6 | 2,4,6-Trinitrophenol | 1.0 | 185–189 | 1.5 |
| 7 | 3-Chloro-2,6-dinitrophenol | 0.87 | 186–189 | 2.4 |
| 8 | 3-Chloro-4,6-dinitrophenol | 0.87 | 187–189 | 2.4 |
| 9 | 4-Cyano-2-iodo-6-nitrophenol | 1.2 | 187–189 | 1.9 |
| 10 | 2-Carbethoxy-4,6-dinitrophenol | 0.98 | 185–188 | 1.9 |
| 11 | 4-Fluoro-2,6-dinitrophenol | 0.8 | 186–189 | 1.5 |
| 12 | 2,6-Dicyano-4-nitrophenol | 0.76 | 186–189 | 2.9 |

2,6-Dicyano-4-nitro-phenol, used in Example 12, was prepared according to generally known processes: 2,6-dicyano-4-nitro-aniline is converted by a Sandmeyer reaction into 2,6-dicyano-4-nitro-chlorobenzene of melting point 218°–219.5°C, reacted with methanol/-sodium hydroxide to give 2,6-dicyano-4-nitro-anisole of melting point 144°–148°C, and the latter subsequently split with sodium iodide in dimethylformamide to give 2,6-dicyano-4-nitro-phenol of melting point 228°–231°C. The last two stages correspond to a process indicated in Belgian Pat. No. 764,117.

EXAMPLE 13

10 g of penicillin-V-sulphoxide p-nitrobenzyl ester (0.02 mol) in 40 ml of benzene, 40 ml of cyclohexane and 60 ml of dimethylacetamide are heated with 1.8 g of 2-chloro-4,6-dinitro-phenol for 12 hours under a water separator, the mixture is concentrated in vacuo at 90°C and 10 ml of methanol are added to the residue. 6.1 g (63%) of 7-phenoxyacetamido-3-methyl-66$^3$-cephem4-carboxylic acid p-nitrobenzyl ester of melting point 185°–188°C crystallize out.

EXAMPLE 14

5 g of penicillin-V-sulphoxide p-nitrobenzyl ester (0.01 mol) in 80 ml of chlorobenzene and 60 ml of dimethylacetamide are heated with 870 mg of 2-chloro-4,6-dinitro-phenol for 5 hours to 120°C, the mixture is concentrated in vacuo, 5 ml of methanol are added and the product is filtered off and washed with methanol/acetonitrile. Yield: 2.7 g (56%) of 7-phenoxyacetamido-3-methyl-$\Delta^3$-cephem-4-carboxylic acid p-nitrobenzyl ester of melting point 187°–190°C.

EXAMPLE 15

10 g of penicillin-V-sulphoxide p-nitrobenzyl ester (0.02 mol) in 75 ml of isoamyl acetate, 75 ml of cyclohexane and 30 ml of dimethylacetamide are heated with 1.74 g of 2-chloro-4,6-dinitro-phenol for 5 hours under reflux, the mixture is concentrated in vacuo, 10 ml of methanol are added and 5.6 g (58%) of 7-phenoxyacetamido-3-methyl-$\Delta^3$-cephem-4-carboxylic acid p-nitrobenzyl ester of melting point 186°–189°C are isolated.

EXAMPLE 16

5 g of penicillin-V-sulphoxide p-nitrobenzyl ester (0.01 mol) in 60 ml of toluene and 30 ml of methanephosphonic acid dimethyl ester are heated with 870 mg of 2-chloro-4,6-dinitro-phenol for 4 hours under reflux, 100 ml of toluene are added and the mixture is twice extracted with 50 ml of water at a time. The toluene phase is dried with sodium sulphate and concentrated in vacuo and 10 ml of methanol are added to the brown residue. The crystals which precipitate are filtered off and washed with methanol/acetonitrile. Yield: 2.7 g (56%) of 7-phenoxyacetamido-3-methyl-$\Delta^3$-cephem-4-carboxylic acid p-nitrobenzyl ester of melting point 185°–187°C.

EXAMPLE 17

5 g of penicillin-V-sulphoxide p-nitrobenzyl ester (0.01 mol) in 90 ml of isoamyl acetate are boiled with 870 mg of 2-chloro-4,6-dinitro-phenol for 5 hours under reflux, the mixture is concentrated in vacuo at 70°C and the crystalline residue is treated with 5 ml of methanol, filtered off and washed with methanol. Yield: 2 g (40%) of 7-phenoxyacetamido-3-methyl-$\Delta^3$-cephem-4-carboxylic acid p-nitrobenzyl ester of melting point 186-190°C.

EXAMPLE 18

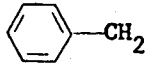

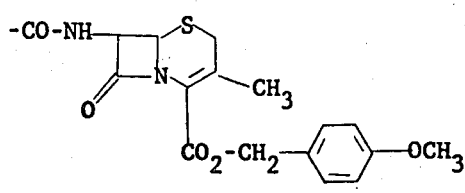

2.35 g of penicillin-G-sulphoxide p-methoxybenzyl ester in 30 ml of toluene and 15 ml of dimethylacetamide are heated with 0.5 g of 2-bromo-4,6-dicyanophenol for 5 hours under reflux, the mixture is concentrated in vacuo at 90°C and 5 ml of methanol are added. The jelly which precipitates is filtered off, pressed out on clay and recrystallized from methanol/active charcoal. Yield: 1.8 g (79.6%) of 7-phenylacetamido-3-methyl-$\Delta^3$-cephem-4-carboxylic acid p-methoxybenzyl ester of melting point 165°–167°C.

EXAMPLE 19

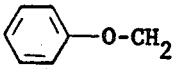

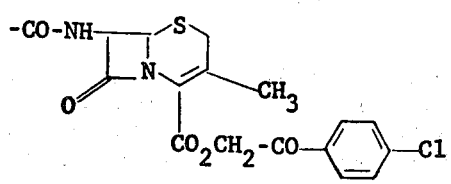

2.43 g of penicillin-V-sulphoxide p-chlorophenacyl ester on 30 ml of toluene and 15 ml of dimethylacetamide are heated with 0.3 g of 2-chloro-4,6-dinitro-phenol for 5 hours under reflux, the mixture is concentrated in vacuo at 90°C and 5 ml of methanol are added. The crystals which precipitate were filtered off after 1 day and washed with methanol. Yield: 1.1 g (47%) of 7-phenoxyacetamido-3-methyl-$\Delta^3$-cephem-4-carboxylic acid p-chlorophenacyl ester of melting point 185°–187°C (from ethanol).

EXAMPLE 20

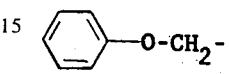

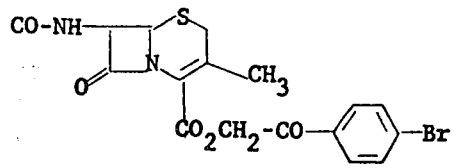

2.65 of penicillin-V-sulphoxide p-bromophenacyl ester in 30 ml of toluene and 15 ml of dimethylacetamide are heated with 0.3 g of 2-bromo-4,6-dicyanophenol for 5 hours under reflux, the mixture is concentrated in vacuo at 90°C and the oily residue is dissolved in a little toluene/ethyl acetate (2:1) and chromatographed with toluene/ethyl acetate (2:1) on a silica gel column. The fractions containing the rearrangement product were concentrated and stirred with a little methanol, and the crystals which precipitate were isolated. Yield: 0.9 g (35%) of 7-phenoxyacetamido-3-methyl-$\Delta^3$-cephem-4-carboxylic acid p-bromophenacyl ester of melting point 177°–181°C.

EXAMPLE 21

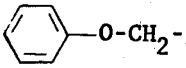

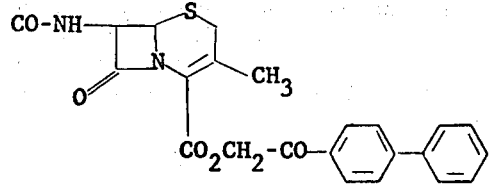

2.65 g of penicillin-V-sulphoxide p-phenylphenacyl ester in 30 ml of toluene and 15 ml of dimethylacetamide are heated with 0.3 g of 2-bromo-4,6-dicyanophenol for 5 hours under reflux, the mixture is cooled, 50 ml of toluene and 50 ml of water are added and the organic phase is separated off and dried with sodium sulphate. The filtrate is concentrated to 2.6 g and 5 ml of methanol are added. The crystals which precipitate are isolated, washed with methanol and dried. Yield: 1.5 g (58.8%) of 7-phenoxyacetamido-3-methyl-$\Delta^3$-cephem-4-carboxylic acid p-phenylphenacyl ester of melting point 184°–185°C. The infra-red spectrum and nuclear resonance spectrum confirm the structure shown.

Penicillin-V-sulphoxide p-phenylphenacyl ester can be prepared as follows:

13 g of penicillin-V-sulphoxide-acid, 5.25 ml of triethylamine and 9.6 g of 4-bromoacetyl-biphenyl in 100 ml of acetone are stirred for 4 hours at room temperature and the reaction mixture is then stirred with 250 ml of water. The viscous oil which first precipitates has crystallized throughout after about 1 hour and is isolated and washed with water. Yield: 17.1 g (87.5%) of penicillin-V-sulphoxide p-phenylphenacyl ester of melting point 163°–164°C (from acetonitrile).

What is claimed is:

1. A process for the production of a 7-acylamino-desacetoxy-cephalosporanic acid ester of the formula:

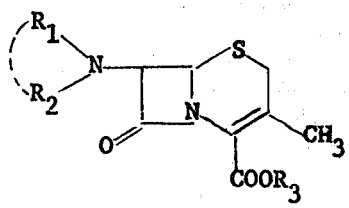

wherein
R₁ is hydrogen, and
R₂ is phenacetyl, phenoxyacetyl, trityl, thienylacetyl, tert.-butoxycarbonyl or α-aminophenacetyl in which the amino moiety is protected, and the phenyl ring is unsubstituted or substituted by hydroxyl, lower alkoxy, lower alkylmercapto or halogen; or
R₁ and R₂ together with the nitrogen atom to which they are attached are phthalimido or succinimido; and
R₃ is benzyl, methoxybenzyl, nitrobenzyl, diphenylmethyl, trityl, β,β,β-trichloroethyl, cyanomethyl, 9-fluorenyl, tert.-butyl, phenacyl, chlorophenacyl, bromophenacyl, nitrophenacyl, phenylphenacyl, alkoxyphenacyl or trimethylsilyl, which comprises the steps of heating a 6-aminopenicillanic acid-sulfoxide-ester of the formula:

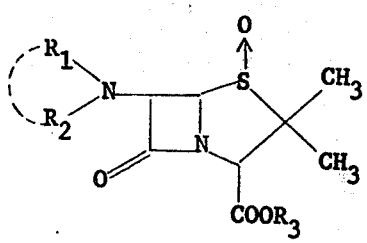

wherein R₁, R₂ and R₃ are as above defined, at temperatures of from 60°C to 150°C in the presence of from 5 to 80 mol % of a phenol of the formula:

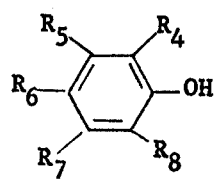

wherein R₄, R₅, R₆, R₇ and R₈ are the same or different and each is selected from the group consisting of hydrogen, nitro, cyano, halogen, perhaloalkyl of 1 to 4 carbon atoms, carbalkoxy of 2 to 5 carbon atoms, or phenylsulphonyl, only one of R₄, R₅, R₆, R₇ and R₈ being halogen and not more than two of R₄, R₅, R₆, R₇ and R₈ being hydrogen, and recovering the compound produced.

2. A process according to claim 1 wherein
R₁ is hydrogen;
R₂ is phenacetyl, phenoxyacetyl, or α-aminophenacetyl in which the amino group is protected; and
R₃ is benzyl, p-methoxybenzyl, p-nitrobenzyl, β,β,β-trichloroethyl, cyanomethyl, p-chlorophenacyl, p-nitrophenacyl, or p-phenylphenacyl.

3. A process according to claim 1 wherein the 6-aminopenicillanic acid-sulfoxide ester is phenoxymethylpenicillin sulphoxide p-nitrobenzyl ester.

4. A process according to claim 1 wherein the temperatures are from 80°C to 130°C.

5. A process according to claim 1 wherein the heating takes place in the presence of a diluent.

6. A process according to claim 5 wherein the diluent is a mixture comprising a weakly polar or non-polar solvent and a strongly polar solvent.

7. A process according to claim 1 wherein the phenol is present in an amount of 20–50 mol% based on the ester of formula II.

8. A process according to claim 1 wherein two of R₄–R₈ are hydrogen.

9. A process according to claim 1 wherein not more than two of R₄, R₅, R₆, R₇ and R₈ are hydrogen and the rest are the same or different and each is selected from the group consisting of nitro, cyano, halogen, trifluoromethyl, carbomethoxy, carbethoxy and phenylsulphonyl.

10. A process according to claim 1 wherein not more than two of R₄, R₅, R₆, R₇ and R₈ are hydrogen and the rest are the same or different and each is selected from the group consisting of nitro, cyano, halogen, trifluoromethyl, carbomethoxy, carbethoxy and phenylsulphonyl.

11. A process according to claim 1 wherein the phenol is 2-bromo-4,6-dicyano-phenol, 2-iodo-4,6-dicyano-phenol, 2-trifluoromethyl-4,6-dinitro-phenol, 2,4-bis-trifluoromethyl-6-nitrophenol, 2,4,6-trinitro-phenol, 2-chloro-4,6-dinitro-phenol, 3-chloro-2,6-dinitro-phenol, 3-chloro-4,6-dinitro-phenol, 4-cyano-2-iodo-6-nitro-phenol, 2-carbethoxy-4,6-dinitro-phenol, 4-carbomethoxy-2,6-dinitro-phenol, 4-fluoro-2,6-dinitro-phenol, 2,6-dicyano-4-nitro-phenol, or 2,4,6-tricyano-3,5-di-(phenylsulphonyl)-phenol.

12. A process according to claim 1 wherein
R₁ is hydrogen;
R₂ is phenoxyacetyl, or phenylacetyl;
R₃ is nitrobenzyl, methoxybenzyl, chlorophenacyl, bromophenacyl, or phenylphenacyl; the reaction temperature is from 80°C to 130°C, and the phenol catalyst is 2-bromo-4,6-dicyano-phenol, 2-iodo-4,6-dicyano-phenol, 2-trifluoromethyl-4,6-dinitro-phenol, 2,4-bis-trifluoromethyl-6-nitro-phenol, 2,4,6-trinitro-phenol, 2-chloro-4,6-dinitro-phenol, 3-chloro-2,6-dinitro-phenol, 3-chloro-4,6-dinitro-phenol, 4-cyano-2-iodo-6-nitro-phenol, 2-carbethoxy-4,6-dinitro-phenol, 4-carbomethoxy-2,6-dinitro-phenol, 4-fluoro-2,6-dinitro-phenol, 2,6-dicyano-4-nitro-phenol, or 2,4,6-tricyano-3,5-di-(phenylsulphonyl)-phenol.

13. A process according to claim 1 for the production of 7-phenoxyacetamido-3-methyl-Δ³-cephem-4-carboxylic acid p-nitrobenzyl ester which comprises the steps of heating penicillin-V-sulphoxide p-nitrobenzyl ester in the presence of 2-bromo-4,6-dicyano-phenol, and recovering the compound produced.

14. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 2-chloro-4,6-dinitro-phenol, and recovering the compound produced.

15. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 4-carbomethoxy-2,6-dinitrophenol, and recovering the compound produced.

16. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 2-trifluoromethyl-4,6-dinitrophenol, and recovering the compound produced.

17. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 2,4-bis-trifluoromethyl-6-nitrophenol, and recovering the compound produced.

18. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 2,4,6-trinitrophenol, and recovering the compound produced.

19. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 3-chloro-2,6-dinitrophenol, and recovering the compound produced.

20. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 3-chloro-4,6-dinitrophenol, and recovering the compound produced.

21. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 4-cyano-2-iodo-6-nitrophenol, and recovering the compound produced.

22. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 2-carbethoxy-4,6-dinitrophenol, and recovering the compound produced.

23. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 4-fluoro-2,6-dinitrophenol, and recovering the compound produced.

24. A process according to claim 1 for the production of 7-phenoxyacetamido-3-methyl-$\Delta^3$-cephem-4-carboxylic acid p-nitrobenzyl ester which comprises the steps of heating penicillin-V-sulphoxide p-nitrobenzyl ester in the presence of 2,6-dicyano-4-nitrophenol, and recovering the compound produced.

25. A process according to claim 1 for the production of 7-phenylacetamido-3-methyl-$\Delta^3$-cephem-4-carboxylic acid p-methoxybenzyl ester which comprises the steps of heating penicillin-G-sulphoxide p-methoxybenzyl ester in the presence of 2-bromo-4,6-dicyano-phenol, and recovering the compound produced.

26. A process according to claim 1 for the production of 7-phenoxyacetamido-3-methyl-$\Delta^3$-cephem-4-carboxylic acid p-chlorophenacyl ester which comprises the steps of heating penicillin V-sulphoxide p-chlorophenacyl ester in the presence of 2-chloro-4,6-dinitrophenol, and recovering the compound produced.

27. A process according to claim 1 for the production of 7-phenoxyacetamido-3-methyl-$\Delta^3$-cephem-4-carboxylic acid p-bromophenacyl ester which comprises the steps of heating penicillin-V-sulphoxide p-bromophenacyl ester in the presence of 2-bromo-4,6-dicyanophenol, and recovering the compound produced.

28. A process according to claim 1 for the production of 7-phenoxyacetamido-3-methyl-$\Delta^3$-cephem-4-carboxylic acid p-phenylphenacyl ester which comprises the steps of heating penicillin-V-sulphoxide p-phenylphenacyl ester in the presence of 2-bromo-4,6-dicyanophenol, and recovering the compound produced.

* * * * *